United States Patent
Kobayashi et al.

(10) Patent No.: US 10,184,109 B2
(45) Date of Patent: Jan. 22, 2019

(54) METHOD FOR OBTAINING DIFFERENTIATED CELLS AND/OR DIFFERENTIATED CELL PRODUCTS FROM UNDIFFERENTIATED CELL AND A METHOD OF PERFUSION CULTURE

(71) Applicant: SYSMEX CORPORATION, Kobe-shi, Hyogo (JP)

(72) Inventors: Eiji Kobayashi, Wakayama (JP); Toshiyuki Sato, Kobe (JP); Kenji Akama, Kobe (JP); Nobuyasu Hori, Kobe (JP); Masaki Shibayama, Kobe (JP); Yuki Aihara, Kobe (JP); Masakazu Kadowaki, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 0 days.

(21) Appl. No.: 14/673,199

(22) Filed: Mar. 30, 2015

(65) Prior Publication Data

US 2015/0275176 A1     Oct. 1, 2015

(30) Foreign Application Priority Data

Mar. 31, 2014 (JP) ................... 2014-072092
Jan. 29, 2015 (JP) ................... 2015-015746

(51) Int. Cl.
*A01N 1/02* (2006.01)
*C12N 5/073* (2010.01)
(Continued)

(52) U.S. Cl.
CPC ......... *C12N 5/0644* (2013.01); *C12N 5/0652* (2013.01); *C12N 5/0663* (2013.01);
(Continued)

(58) Field of Classification Search
CPC .. C12N 5/0644; C12N 5/0652; C12N 5/0663; C12N 2506/1353; C12N 2506/11;
(Continued)

(56) References Cited

U.S. PATENT DOCUMENTS

| 5,338,662 A | * | 8/1994 | Sadri | .......... | A01N 1/02 435/284.1 |
| 8,268,621 B2 | | 9/2012 | Turovets et al. | | |

(Continued)

FOREIGN PATENT DOCUMENTS

| JP | 2002-171865 A | | 6/2002 |
| JP | 2002171865 | * | 6/2002 |

(Continued)

OTHER PUBLICATIONS

Uygun et al. Organ reengineering through development of a transplantable recellularized liver graft using decellularized liver matrix. Nature Medicine (2010), v16(7), p. 814-820 and appended Online Methods.*

(Continued)

*Primary Examiner* — Sean C. Barron
(74) *Attorney, Agent, or Firm* — Sughrue Mion, PLLC (57) ABSTRACT

Disclosed is a method for obtaining differentiated cells and/or differentiated cell products, including the steps of: introducing undifferentiated cells into a perfused organ or living tissue; subjecting the undifferentiated cells introduced to perfusion culture together with the organ or living tissue so as to allow the undifferentiated cells to differentiate, thereby obtaining differentiated cells and/or differentiated cell products; collecting a perfusion culture solution that contains the resulting differentiated cells and/or differentiated cell products; and obtaining the differentiated cells (Continued)

and/or differentiated cell products contained in the collected perfusion culture solution.

17 Claims, 4 Drawing Sheets

Specification includes a Sequence Listing.

(51) Int. Cl.
  C12N 5/074  (2010.01)
  C12N 5/077  (2010.01)
  C12N 5/078  (2010.01)
  C12N 5/0775  (2010.01)

(52) U.S. Cl.
  CPC .......... A01N 1/0247 (2013.01); C12N 5/0603 (2013.01); C12N 5/0607 (2013.01); C12N 5/0696 (2013.01); C12N 2506/11 (2013.01); C12N 2506/1353 (2013.01)

(58) Field of Classification Search
  CPC .............. C12N 5/0068; C12N 2503/02; C12N 2533/90; C12N 5/0607; C12N 5/0603; A01N 1/0247
  USPC ................... 435/1.2, 6.13, 377, 366, 370, 29
  See application file for complete search history.

(56) References Cited

U.S. PATENT DOCUMENTS

| | | | |
|---|---|---|---|
| 2006/0182724 A1 | 8/2006 | Riordan | |
| 2012/0064537 A1* | 3/2012 | Ross | C12N 5/0068 435/6.13 |
| 2012/0282228 A1* | 11/2012 | Bhasin | C12N 5/0607 424/93.7 |
| 2012/0315338 A1 | 12/2012 | Li et al. | |
| 2013/0017533 A1* | 1/2013 | Tsuji | A01N 1/0247 435/1.2 |

FOREIGN PATENT DOCUMENTS

| | | |
|---|---|---|
| JP | 2004-135625 A | 5/2004 |
| JP | 2012-19690 A | 2/2012 |
| JP | 2013-75888 A | 4/2013 |
| WO | 02064755 A2 | 8/2002 |
| WO | 2005068610 A1 | 7/2005 |
| WO | 2007/025233 A1 | 3/2007 |

OTHER PUBLICATIONS

Pereira et al. Gallstone Dissolution with Oral Bile Acid Therapy. Digestive Diseases and Sciences, v42(8), p. 1775-1782.*
Carraro et al. A Combining Method to Enhance the In Vitro Differentiation of Hepatic Precursor Cells. Tissue Engineering Part C (2010), v16(6), p. 1543-1551.*
Herrera et al. Isolation and Characterization of a Stem Cell Population from Adult Human Liver. Stem Cells (2006), v24, p. 2840-2850.*
Li et al. Induced bone marrow mesenchymal stem cells improve cardiac performance of infarcted rat hearts. Mol Biol Rep (2012), v39, p. 1333-1342.*
Liao et al. The continuing evolution of the Langendorff and ejecting murine heart: new advances in cardiac phenotyping. Am J Physiol Heart Circ Physiol (2012), v303, H156-H167.*
Toth et al. Relaxin stimulates atrial natriuretic peptide secretion in perfused rat heart. J Endocrinol.(1996), v150(3), p. 487-495.*
Y. Saito. Roles of atrial natriuretic peptide and its therapeutic use. Journal of Cardiology (2010), v56, p. 262-270.*
J.W. Starnes. Effect of storage conditions on lactate dehydrogenase released from perfused hearts. International Journal of Cardiology (2008), v127, p. 114-116.*
Lin et al. Allogeneic and Xenogeneic Transplantation of Adipose-Derived Stem Cells in Immunocompetent Recipients Without Immunosuppressants. (Stem Cells and Development (2012), v21(15), p. 2770-2778. (Year: 2012).*
Badylak et al. Whole-Organ Tissue Engineering: Decellularization and Recellularization of Three-Dimensional Matrix Scaffolds. Annu. Rev. Biomed. Eng. 2011. 13:27-53. (Year: 2011).*
Amedeo Carraro et al: "Combining Method to Enhance the In Vitro Differentiation of Hepatic Precursor Cells", Tissue Engineering Part C: Methods, vol. 16, No. 6, (2010), pp. 1543-1551.
CJ. Danpure, "Lactate dehydrogenase and cell injury", Jul. 1984, pp. 144-148, vol. 2, Cell Biochemistry and Function.
Jan Bakker, MD. et al., "Serial blood lactate levels can predict the development of multiple organ failure following septic shock", The American Journal of Surgery, Feb. 1996, pp. 221-226, vol. 171, Issue 2.
Robert Fleischaker, et al., "Oxygen demand and supply in cell culture", Dec. 1, 1981, pp. 193-197, vol. 12, Issue 4, European journal of applied microbiology and biotechnology, Springer-Verlag.
"Experimental Study on Mouse Embryonic Stem Cells Differentiation Induced by Kidney", Kuroba Million Degree Thesis Database Study, Huanglin Million Degree Thesis Data 1-73 (Huang 2010).

* cited by examiner

SPECIMEN: 3-A
ACQUISITION DATE: 6/23/2014   ACCELERATING VOLTAGE: 80 kv
ACQUISITION TIME: 2:00:04 PM   INDICATED MAGNIFICATION: 25 kx

FIG. 6

METHOD FOR OBTAINING DIFFERENTIATED CELLS AND/OR DIFFERENTIATED CELL PRODUCTS FROM UNDIFFERENTIATED CELL AND A METHOD OF PERFUSION CULTURE

CROSS REFERENCE TO RELATED APPLICATIONS

This application claims priority from prior Japanese Patent Application No. 2014-072092, filed on Mar. 31, 2014, entitled "METHOD FOR OBTAINING A DIFFERENTIATED CELL", and Japanese Patent Application No. 2015-015746, filed on Jan. 29, 2015, the contents of all of which are incorporated herein by reference in their entirety.

TECHNICAL FIELD

The present invention relates to a method for obtaining differentiated cells and/or differentiated cell products from undifferentiated cells and a method of perfusion culture.

BACKGROUND

Technologies for differentiating undifferentiated cells such as stem cells into desired cells are expected to be adaptable to regenerative medicine and screening of prophylactic/therapeutic drugs for various diseases.

Conventionally, there are known methods for obtaining differentiated cells or products thereof from stem cells in vitro or in vivo.

For example, a method for obtaining differentiated cells or products thereof in vitro is described in U.S. Pat. No. 8,268,621, Japanese Unexamined Patent Publication No. 2004-135625 or US Patent Publication No. 2012/0315338.

U.S. Pat. No. 8,268,621 describes a method of producing primary germ layer cells, comprising: culturing embryonic stem cells or the like in the presence of an agent that alters the epigenetic state of cell such as a demethylation agent (5-azacytidine, 5-aza-2' deoxycytidine, etc.) or a histone deacetylase inhibitor; and culturing the embryonic stem cells in the presence of various growth factors or cytokines.

Japanese Unexamined Patent Publication No. 2004-135625 describes a method for inducing the differentiation of somatic stem cells into somatic cells, comprising co-culturing desired tissue- and organ-derived cells with the somatic stem cells. In the method disclosed in the patent document, it is necessary to prepare desired tissue- and organ-derived cells after differentiation for co-culture.

US Patent Publication No. 2012/0315338 describes a method of generating megakaryocytes by culturing hemangioblasts in a medium containing various growth factors or cytokines and a method of generating platelets by culturing the generated megakaryocytes.

A method for obtaining a differentiated cell or a product thereof in vivo is described in, for example, Japanese Unexamined Patent Publication No. 2002-171865.

Japanese Unexamined Patent Publication No. 2002-171865 describes a method for producing human organ cells, comprising: introducing human-derived organ cells or organ stem cells through a duct of an animal other than humans; transplanting the human-derived organ cells or organ stem cells into a specific site of the animal other than humans; allowing the cells to grow and differentiate; and collecting the resultant human-derived organ cells. The patent document describes that the transplanted organ cells or organ stem cells are allowed to grow to a certain level, and the use of, for example, a fluorescence-activated cell sorter (FACS) enables human cells to be separated from animal cells according to differences of surface antigens.

WO 2007/025233 describes a method of making a solid organ to be transplanted into a patient by using stem cells. The patent document describes a method for producing an organ, comprising: perfusing an organ with a cell disruption medium containing a surfactant to form a decellularized organ; and bringing the decellularized organ into contact with populations of regenerated cells such as mesenchymal stem cells (MSC), under conditions such that the regenerated cells are allowed to engraft, grow, and/or differentiate inside or on the surface of the decellularized organ.

Japanese Unexamined Patent Publication No. 2012-019690 describes a method for evaluating whether or not stem cells can differentiate into cells forming a desired tissue in vivo. In the method described in the patent document, the stem cells to be evaluated are transplanted into a desired tissue anlage of a non-human mammal, and then the tissue anlage is cultured in vitro. The possibility of differentiation of the stem cells into cells forming the tissue in vivo is determined by using the level of distribution of the cells, in the tissue anlage, derived from the transplanted stem cells as an indicator.

Although the method described in U.S. Pat. No. 8,268,621 and the method described in US Patent Publication No. 2012/0315338 describe a method for obtaining differentiated cells or products thereof by culturing stem cells in a medium containing a predetermined substance, culture conditions are complicated because it is necessary to subculture the cultured cells multiple times.

In the method described in Japanese Unexamined Patent Publication No. 2004-135625, it is necessary to prepare differentiated cells for co-culture, in order to allow stem cells to differentiate. Accordingly, in the case where it is difficult to obtain differentiated cells or to culture differentiated cells, it is not resultantly possible to allow the stem cells to differentiate into target cells.

In the method of obtaining differentiated cells from stem cells in vivo as disclosed in Japanese Unexamined Patent Publication No. 2002-171865, it is inevitable that the differentiated cells to be obtained are mixed with host cells. Consequently, the subsequent purification process becomes a burden.

In WO 2007/025233, it is necessary to perform decellularization by perfusing an organ with a cell disruption medium containing a surfactant, which makes the operation complicated.

The method described in Japanese Unexamined Patent Publication No. 2012-019690 aims at determining whether or not stem cells to be transplanted are suitable for transplantation, and it does not assume the process of collecting differentiated cells.

An object of the present invention is to provide a method for obtaining differentiated cells and/or differentiated cell products from undifferentiated cells, which is a simple operational method and enables differentiated cells to be easily obtained.

SUMMARY OF THE INVENTION

The scope of the present invention is defined solely by the appended claims, and is not affected to any degree by the statements within this summary.

The present inventors have dedicated to repetitive studies to achieve the above object. As a result, they have found that the above object to be achieved by introducing undifferentiated cells into a perfused organ or living tissue and subjecting the undifferentiated cells to perfusion culture together with the organ or living tissue. Accordingly, they have completed the present invention.

Consequently, the present invention provides:

a method for obtaining differentiated cells and/or differentiated cell products, comprising the steps of: introducing undifferentiated cells into a perfused organ or a perfused living tissue; subjecting the undifferentiated cells to perfusion culture together with the organ or living tissue so as to allow the undifferentiated cells to differentiate; collecting a perfusion culture solution comprising the resulting differentiated cells and/or differentiated cell products; and obtaining the differentiated cells and/or differentiated cell products comprised in the collected perfusion culture solution, a method of perfusion culture with a perfusion culture system using a perfused organ or a perfused living tissue, comprising the steps of: measuring an activity of lactate dehydrogenase of a perfusate on a day the organ or the living tissue is extracted, the extracted organ or living tissue being placed in the perfusate; evaluating a storage state of the organ or living tissue is good when a specific activity or activity of the lactate dehydrogenase is lower than a predetermined threshold; and conducting following steps when the storage state of the organ is evaluated to be good in the evaluation step: introducing undifferentiated cells into a perfused organ or a perfused living tissue; subjecting the undifferentiated cells to perfusion culture together with the organ or living tissue so as to allow the undifferentiated cells to differentiate; collecting a perfusion culture solution comprising the resulting differentiated cells and/or differentiated cell products; and obtaining the differentiated cells and/or differentiated cell products comprised in the collected perfusion culture solution, and a method of perfusion culture with a perfusion culture system using a perfused organ or a perfused living tissue, comprising the steps of: introducing undifferentiated cells into a perfused organ or a perfused living tissue, the organ or the living tissue being placed in a perfusion culture solution in a container of the perfusion culture system; subjecting the undifferentiated cells to perfusion culture together with the organ or living tissue in the perfusion culture solution in the container so as to allow the undifferentiated cells to differentiate; collecting the perfusion culture solution comprising the resulting differentiated cells and/or differentiated cell products from the organ or living tissue; and obtaining the differentiated cells and/or differentiated cell products comprised in the collected perfusion culture solution.

The present invention enables a differentiated cell and/or a product thereof to be easily obtained.

DETAILED DESCRIPTION OF THE PREFERRED EMBODIMENTS

The method for obtaining differentiated cells and/or differentiated cell products includes the step of introducing undifferentiated cells into a perfused organ or living tissue.

The term "introducing" means that the undifferentiated cells are placed so as to be in contact with or are brought close to the inside or surface of the organ or the inside or surface of the living tissue. Examples include placing of undifferentiated cells so as to be in contact with an organ or living tissue, and placing of undifferentiated cells and an organ or living tissue so as to be present in the same liquid (i.e., placing of undifferentiated cells and an organ or living tissue in the same liquid). More specific examples include adding of undifferentiated cells to a perfusate and then sending of the undifferentiated cells into an organ or living tissue; infusing or injecting of a liquid containing undifferentiated cells into an organ or living tissue through the artery or vein of the organ or living tissue; and adding of undifferentiated cells to a liquid in which an organ or living tissue has been immersed. In the present embodiment, undifferentiated cells are added to a perfusate so that the undifferentiated cells may be introduced into an organ or living tissue.

The undifferentiated cells are introduced into the perfused organ or living tissue.

The kind of the perfusate is not particularly limited as long as it is appropriate for maintaining cell life. Examples thereof include media (specifically, RPMI medium (Roswell Park Memorial Institute medium), MEM media (Minimum Essential Media), DMEM medium (Dulbecco's Modified Eagle Medium), Ham's F-12 medium, etc.), physiological saline, and organ storage solutions (UW solution (University of Wisconsin solution), ET-Kyoto solution, etc.). The perfusate may contain additives necessary for maintaining cell life such as erythrocytes, plasma, serum and amino acids. The flow rate of the perfusate is not particularly limited as long as it is a flow rate in which the undifferentiated cells introduced do not remain fixed to the organ or living tissue. The flow rate generally used in perfusion of organs or the like may be, for example, 0.01 mL/min or more and 100 mL/min or less, and preferably 0.1 mL/min or more and 20 mL/min or less. The temperature during perfusion is not particularly limited. The temperature may be, for example, 4° C. or higher and 40° C. or lower, preferably 20° C. or higher and 38° C. or lower, and more preferably 35° C. or higher and 37° C. or lower. The perfusion time is not particularly limited. The perfusion time may be, for example, 1 minute or more and 3000 minutes or less, preferably 15 minutes or more and 1500 minutes or less, more preferably 60 minutes or more and 1000 minutes or less, still preferably 100 minutes or more and 800 minutes or less, and still more preferably 200 minutes or more and 600 minutes or less. The term "perfusion time" used herein means the sum total of the time required for perfusion before introduction of the undifferentiated cells.

When the undifferentiated cells are introduced, the perfusion may be stopped. The stopping time may be preferably 0.1 minutes or more and 1200 minutes or less, more preferably 0.1 minutes or more and 500 minutes or less, further preferably 0.1 minutes or more and 200 minutes or less, and still preferably 0.1 minutes or more and 100 minutes or less. The timing of the introduction of the undifferentiated cells in the stopping time is not particularly limited. Usually, the undifferentiated cells may be introduced within 60 minutes, more preferably within 30 minutes, further preferably within 10 minutes, and still preferably within 5 minutes after the perfusion is stopped.

Figure 1:
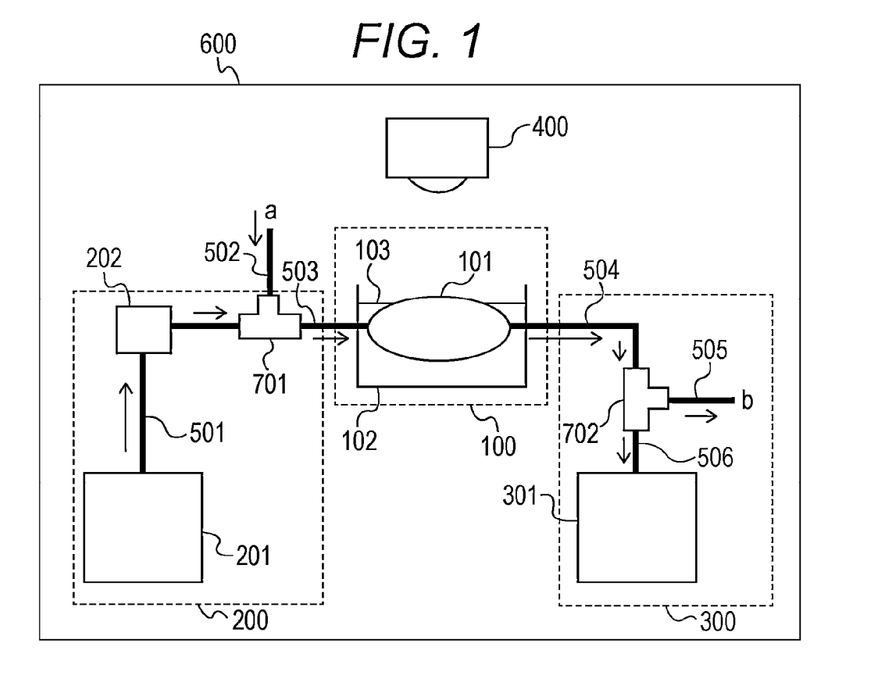
FIG. 1 is a pattern diagram of a perfusion culture system.

In the present embodiment, the undifferentiated cells may be introduced using a perfusion culture system shown in FIG. 1. The perfusion culture system may be mainly configured to include a swine spleen 101 used as an organ or living tissue, a perfusate bottle 201, a liquid feeding pump 202, a drainage bottle 301, tubes 501 to 506 that connect them, and three-way cocks 701 and 702.

In the present embodiment, a solution containing undifferentiated cells is injected from an undifferentiated cell introducing port a that is located at the end of the tube 502, and the solution may enter the three-way cock 701 and the tube 503. Thereafter, the flow rate of the perfusion culture solution is appropriately adjusted so that the undifferentiated cells may be introduced into the swine spleen 101 from the tube 503 connected to the artery of the swine spleen 101 after ligation of short gastric vein and artery. In this process, at the swine spleen 101 side of the tube 503, a layer of air may be formed between the perfusate in the tube 503 which is remained by prior perfusion and the solution containing undifferentiated cells injected into the tube 503. Also at the liquid feeding pump 202 side of the tube 503, a layer of air may be formed between the injected solution containing undifferentiated cells and the perfusion culture solution. In the present embodiment, the flow rate of the perfusion culture solution is appropriately adjusted, whereby the injected solution containing undifferentiated cells may be introduced into the swine spleen 101. This introduction means that the solution is fed until the interface between the injected solution containing undifferentiated cells and the layer of air formed at the liquid feeding pump side reaches the interface between the tube 503 and the artery of the swine spleen 101 connected to the tube. This introduction may be visually confirmed. The flow rate of the perfusion culture solution in the process is not particularly limited as long as it is a flow rate in which the introduction of undifferentiated cells can be visually confirmed. For example, the flow rate may be 0.01 mL/min or more and 100 mL/min or less, and preferably 0.1 mL/min or more and 20 mL/min or less. The introduction process may be carried out preferably after a period of 0 seconds or more and 10 minutes or less, more preferably after a period of 0 seconds or more and 60 seconds or less following the injection of the undifferentiated cells from the introducing port a.

In another embodiment, the solution containing undifferentiated cells is injected from the undifferentiated cell introducing port a located at the end of the tube 502, and the solution may enter the three-way cock 701 and the tube 503. Thereafter, the flow rate of the perfusion culture solution is appropriately adjusted so that the undifferentiated cells may be introduced into the swine spleen 101 from the tube 503 connected to the artery of the swine spleen 101 after ligation of short gastric vein and artery. In the process, the solution containing undifferentiated cells is injected into the tube 503, thereby allowing the perfusate remained by prior perfusion to flow into the spleen. Thereafter, the perfusion culture solution in an amount equal to the amount of the solution containing undifferentiated cells is perfused by the liquid feeding pump 202. As a result, the undifferentiated cells may be introduced into the spleen. The flow rate of the perfusion culture solution in the process is not particularly limited as long as it is a flow rate which can be controlled by the liquid feeding pump depending on the amount of the solution containing undifferentiated cells. For example, the flow rate may be 0.01 mL/min or more and 100 mL/min or less, and preferably 0.1 mL/min or more and 20 mL/min or less. The introduction process may be carried out preferably after a period of from 0 seconds or more and 10 minutes or less, more preferably after a period of from 0 seconds or more and 60 seconds or less following the injection of the undifferentiated cells from the introducing port a.

The undifferentiated cells are not particularly limited as long as they do not reach the final differentiation stage of the embryological cell lineage in vivo. Examples thereof include stem cells and precursor cells. Examples of the stem cells include ES cells (Embryonic Stem cells), clones ES cells, iPS cells (induced Pluripotent Stem cells), MUSE cells (MUltilineage-differentiating Stress Enduring cells), mesenchymal stem cells, neural stem cells, epithelial stem cells, hepatic stem cells, germ stem cells, hematopoietic stem cells, and skeletal muscle stem cells. In particular, iPS cells and mesenchymal stem cells are preferred. The undifferentiated cells are preferably human-derived cells. In the present embodiment, the undifferentiated cells may be mesenchymal stem cells (MSC) derived from human bone marrow.

Examples of the precursor cells include platelet precursor cells, liver precursor cells, heart precursor cells, and neuronal precursor cells. Examples of the platelet precursor cells include megakaryocyte precursor cells, megakaryoblasts, and promegakaryocytes. Examples of the liver precursor cells include hepatoblasts, hepatic precursor cells, hepatic stellate precursor cells, hepatic stem/precursor cells, vascular endothelial precursor cells from liver, and mesothelial precursor cells from liver. Examples of the heart precursor cells include cardiac muscle precursor cells and vascular endothelial precursor cells from heart. Examples of the neuronal precursor cells include neuron precursor cells, glial precursor cells, and vascular endothelial precursor cells from central nervous system. The precursor cells are preferably platelet precursor cells, and in particular preferably megakaryoblasts or promegakaryocytes.

The organ or living tissue is not particularly limited as long as it is suitable for perfusion. The organs or living tissues of animals other than humans, such as swine, mice, and chickens are preferred.

Examples of the organs include heart, liver, lung, skeletal muscle, brain, pancreas, spleen, kidney, small intestine, uterus, and bladder.

Examples of the living tissues include bone, cartilage, joints (e.g., knee, shoulder and hip joint), tracheae, spinal cord, cornea, eyeball, skin, and blood vessel.

The differentiated cells are not particularly limited as long as they have reached the final differentiation stage of the embryological cell lineage in vivo. Specific examples thereof include mature megakaryocytes, osteoblasts, chondrocytes, adipocytes, hepatocytes, hepatic mesothelial cells, biliary epithelial cells, hepatic stellate cells, hepatic sinusoid endothelial cells, Kupffer cells, pit cells, vascular endothelial cell, pancreatic duct epithelial cells, pancreatic duct cells, centroacinous cells, acinar cells, islets of Langerhans, cardiac muscle cells, fibroblasts, smooth muscle cells, type I alveolar epithelial cells, type II alveolar epithelial cells, Clara cells, ciliated epithelial cells, basal cells, goblet cells, neuroendocrine cells, kultschitzky cells, renal tubular epithelial cells, urothelial cells, columnar epithelial cells, glomerular epithelial cells, glomerular endothelial cells, podocytes, mesangium cells, nerve cells, astrocytes, microglia, and oligodendrocytes.

The differentiated cells are preferably cells allogeneic to the cells forming the organ or living tissue used for culture. The allogeneic cells are different from a cell group forming the organ or living tissue used for culture and precursor cells or somatic stem cells present in the cell lineage leading to constituent cells. A cell group forming the organ or living tissue means a group of cells forming the organ or living tissue itself, except for cells which do not substantially form the organ or living tissue, such as cells contained in blood.

In the present embodiment, a swine spleen may be used as the organ or living tissue. In the present embodiment, the differentiated cells may be osteoblasts allogeneic to spleen cells.

Syngeneic cells means that the collected cells are the same as a cell group forming the organ or living tissue used for culture and precursor cells or somatic stem cells present in the cell lineage leading to constituent cells.

In the present embodiment, the spleen may be used as the organ or living tissue. In this case, the syngeneic cells may be cells syngeneic to spleen-forming cells, for example, intrasplenic cells or spleen endothelial cells.

The differentiated cell products are substances produced by the function of the differentiated cells. For example, in the case where the differentiated cells are mature megakaryocytes, the differentiated cell products may be platelets because the mature megakaryocytes have a platelet-producing ability. Examples of the differentiated cell products include, in addition to platelets produced from mature megakaryocytes, bile produced from hepatocytes.

The undifferentiated cells thus introduced are subjected to perfusion culture together with the organ or living tissue so as to allow the undifferentiated cells to differentiate, thereby obtaining differentiated cells and/or differentiated cell products.

The perfusion culture is not particularly limited and may be performed by any method known to those skilled in the art.

The kind of the perfusion culture solution is not particularly limited, and examples thereof include RPMI medium (Roswell Park Memorial Institute medium), MEM medium (Minimum Essential Media), DMEM medium (Dulbecco's Modified Eagle Medium), and Ham's F-12 medium. The perfusion culture solution may contain additives necessary for maintaining cell life such as erythrocytes, plasma, serum and amino acids. The flow rate of the perfusion culture solution is not particularly limited as long as it is generally used in perfusion of organs or the like. For example, the flow rate may be 0.01 mL/min or more and 100 mL/min or less, and preferably 0.1 mL/min or more and 20 mL/min or less. The temperature during perfusion is not particularly limited. The temperature may be, for example, 4° C. or higher and 40° C. or lower, preferably 20° C. or higher and 38° C. or lower, and more preferably 35° C. or higher and 37° C. or lower. The perfusion culture time is not particularly limited. The perfusion culture time may be, for example, 0.01 hours or more and 100 hours or less, preferably 0.1 hours or more and 10 hours or less, more preferably 0.1 hours or more and 3 hours or less. The term "perfusion culture time" used herein means the sum total of the time required for perfusion culture after introduction of the undifferentiated cells.

The perfusion culture solution may be the same as the perfusate used to perfuse the organ or living tissue before introduction of the undifferentiated cells. In this case, the flow rate and temperature of the perfusion culture solution may be identical to those of the perfusate used to perfuse the organ or living tissue before introduction of the undifferentiated cells.

In the perfusion culture, the liquid-feeding process may be stopped. In this case, the term "perfusion culture time" means the sum total of the time required for perfusion culture after introduction of the undifferentiated cells and the time required for stopping the liquid-feeding process. The stopping time of the liquid-feeding process is not particularly limited as long as it does not prevent cells differentiated by perfusion culture and/or differentiated cell products from being obtained. The stopping time may be preferably 0.01 hours or more and 100 hours or less, more preferably 0.1 hours or more and 10 hours or less, and further preferably 0.1 hours or more and 3 hours or less following the introduction of the undifferentiated cells into the organ or living tissue. The timing of stopping the liquid-feeding process is not particularly limited. For example, the timing may be the same as that of the case of introducing the undifferentiated cells into the organ or living tissue. Alternatively, the timing may be after a period of 0.01 seconds or more and 1000 seconds or less, preferably a period of 0.1 seconds or more and 100 seconds or less, more preferably after 60 seconds, further preferably after 30 seconds, and still preferably after 10 seconds following the introduction of the undifferentiated cells into the organ or living tissue.

Then, the perfusion culture solution is collected. The method for collecting the perfusion culture solution is not particularly limited, and any method known to those skilled in the art may be used. Examples of the method include pouring the perfusion culture solution into a container, such as a test tube, from a tube connected to the organ or living tissue.

In the present embodiment, the perfusion culture solution may be collected from a collection port b located at the end of a tube 505 connected to the three-way cock 702 that connects the swine spleen 101 and the drainage bottle 301 in the perfusion culture system shown in FIG. 1.

The differentiated cells and/or differentiated cell products contained in the collected perfusion culture solution are obtained. The method for obtaining the differentiated cells and/or differentiated cell products is not particularly limited, and any method known to those skilled in the art may be appropriately selected and used. Examples of the method include centrifugation, filtration, and chromatography.

For example, in the case where mature megakaryocytes are collected as the differentiated cells, centrifugation or the like is performed under suitable conditions, thereby collecting the mature megakaryocytes. In the case where the differentiated cells are mature megakaryocytes, platelets, i.e., products thereof may be collected. In this case, the platelets may be collected by centrifugation or the like under suitable conditions.

Before the introduction step, the step of determining whether or not the operation proceeds to the introduction step by evaluating the storage state of the organ (determination step) may be further performed. When the freshness of the organ is deteriorated, the differentiation-inducing properties of the organ also tend to be reduced. Therefore, the evaluation of the storage state (freshness) of the organ may be an indicator showing whether or not the organ maintains desired differentiation-inducing properties, namely, whether or not a sufficient amount of desired differentiated cells and/or differentiated cell products can be obtained by using the organ. In the case where the storage state of the organ is evaluated to be good, the operation proceeds to the introduction step. In the case where the storage state of the organ is evaluated to be not good, the steps after the introduction step may be determined not to be performed. Even in the case where the storage state of the organ is evaluated to be not good, it is possible to perform the steps after the introduction step using the organ. However, in this case, a sufficient amount of desired differentiated cells and/or differentiated cell products may not be obtained. Under such circumstance, it is preferable to replace the organ evaluated as not-good storage state with a fresh organ.

The determination step may be carried out, for example, by measuring the activity and/or concentration of at least one marker reflecting the freshness of the organ, and comparing a measured value and/or a value obtained based on the measured value (e.g., a ratio) to the standard. Examples of such a marker include cell death markers known to those skilled in the art, such as amount, concentration, activity value, and specific activity value of lactate dehydrogenase (LDH), amount and concentration of lactic acid, perfusion pressure, and dissolved oxygen amount. In the case where the perfusion pressure is used as an indicator, a variation between the water pressure of the perfusate upon introducing the perfusate into the organ and the water pressure of the perfusate upon ejecting the perfusate from the organ (e.g., a difference or a ratio) may be used. The use of LDH as a cell death marker is described in, for example, "Cell Biochemistry and Function (1984) No. 2, Vol. 3, p. 144-148". The use of lactic acid as a cell death marker is described in, for example, "The American Journal of Surgery (1996) No. 171, Vol. 2, 221-226". The use of perfusion pressure as a cell death marker is described in, for example, Japanese Unexamined Patent Publication No. 2013-75888. The use of dissolved oxygen as a cell death marker is described in, for example, "European Journal of Applied Microbiology and Biotechnology (1981) No. 12, p. 193-197". The standards for the above markers may be measured values as they are such as activities and/or concentrations of the markers on the day of extraction of the organ to be evaluated, or values such as activities and/or concentrations of the markers measured on the day of extraction of a plurality of organs (e.g., averages or ratios).

In the present embodiment, in the case where the lactate dehydrogenase activity value is used, the determination step may be performed, for example, as follows. First, the organ on the day of extraction is placed in the perfusion culture system of the present embodiment, and the lactate dehydrogenase activity of the perfusate on the day of extraction is measured. The measured value is defined as an activity value A. Next, the lactate dehydrogenase activity of the perfusate is measured before introduction of undifferentiated cells and perfusion culture (e.g., a few days after the extraction). The measured value is defined as an activity value B. Both of the activity values A and B are preferably measured before introduction of undifferentiated cells. The determination step may be carried out by evaluating the storage state of the organ based on the variation of the activity values A and B (e.g., the activity value A-the activity value B, the activity value B/the activity value A). In the case where the ratio (B/A) is preferably 0.51 or more and 1 or less, more preferably 0.61 or more and 1 or less, further preferably 0.71 or more and 1 or less, and still preferably 0.8 or more and 1 or less, the storage state of the organ may be evaluated to be good. In this case, the operation may be determined to proceed to the following introduction step. On the other hand, in the case where the ratio (B/A) is less than 0.5, the storage state of the organ may be evaluated not to be good. In this case of the organ, the operation may be determined not to be able to proceed to the following introduction step or may be determined not to be preferable to proceed to the introducing step. The above-described ratio may be a ratio of the lactate dehydrogenase activity measured on the day of extraction of the same organ to the lactate dehydrogenase activity measured immediately before the use of the organ. The lactate dehydrogenase activity may be measured by any method known to those skilled in the art. In the present embodiment, the measurement of the lactate dehydrogenase activity may be performed by measuring absorptivity at 490 nm.

EXAMPLES

Hereinafter, the present invention will be specifically described with reference to the examples. However, the following examples are merely exemplification of the present invention, and the present invention is not limited to the following examples.

Reference Example 1

Perfusion Culture System of Swine Spleen

The present inventors have constructed a perfusion culture system used in the following examples. As shown in FIG. 1, the perfusion culture system is configured to include a perfusion section 100 which includes an organ or living tissue to be perfused, a liquid feeding section 200 for introducing a perfusion culture solution into the perfusion section 100, a collecting section 300 for collecting the perfusion culture solution discharged from the perfusion section 100, an imaging section 400 for photographing the perfusion section 100, tubes 501 to 506 which connect respective components, an incubator 600 which performs perfusion culture, and three-way cocks 701 and 702 which connect the tubes.

a) Perfusion Section 100

A swine spleen was used herein as an organ or living tissue 101. First, a spleen was extracted from a pig (LWD system, about 30 kg) anesthetized with Ketalar. After ligation of short gastric vein and artery, the artery was cannulated using the tube 503 (Atom Multi-Purpose Tube, manufactured by Atom Medical Corporation, outer diameter: 2.0 mm), and the vein was cannulated using the tube 504 (safeed extension tube, manufactured by TERUMO CORPORATION). Thereafter, 50 mL of physiological saline containing 1 mL of heparin (500 mL) was injected from the tube cannulated to the artery into the cannulated swine spleen 101 through a syringe (for 50 mL, manufactured by TERUMO CORPORATION) at a flow rate of about 20 mL/min. Then, it was confirmed that the introduced physiological saline containing heparin was ejected from the tube cannulated to the vein. Continuously, 50 mL of physiological saline containing heparin was circulated again, followed by cold storage at 4° C. until it was used.

When the swine spleen was used, the swine spleen 101 covered with gauze was immobilized in an open container 102 containing a physiological saline 103. The container was arranged in the incubator 600 (NRB-32A, manufactured by Hitachi, Ltd.) kept at 37° C. Thus, the perfusion section 100 was constructed. The perfusate was injected from the tube 503 cannulated to the artery of the swine spleen 101, and ejected from the tube 504 cannulated to the vein.

b) Liquid Feeding Section 200

The liquid feeding section 200 is mainly configured to include a perfusate bottle 201 (5 L, 2002-5000SD, manufactured by AS ONE Corporation) which is connected to the tube 501 (C-Flex Pump Tube, product number: 6424-25, manufactured by Yamato Scientific Co. Ltd.), and a liquid feeding pump 202 (Master Flex Liquid Feeding Pump 07528-10, manufactured by Yamato Scientific Co. Ltd.) to which the tube 501 is attached. The liquid feeding pump 202 was connected to the swine spleen 101 through the tubes 501 and 503. The three-way cock 701 (R-type, Cock-specification 360°, TS-TR2K, manufactured by TERUMO CORPORATION) was provided between the tubes 501 and 503. The three-way cock 701 thus provided enables undifferentiated cells to be mixed with the perfusate through the tube 502 (C-Flex Pump Tube, product number: 6424-25, manufactured by Yamato Scientific Co. Ltd.) connected to the three-way cock. A perfusion culture solution (RPMI medium; Roswell Park Memorial Institute medium) was put into the perfusate bottle 201. The perfusion culture solution is a solution prepared by adding 10% (final concentration) FBS (manufactured by Hyclone), 50-fold diluted Antibiotic-Antimycotic (15240-062, manufactured by Gibco), and 2 mM (final concentration) L-Glutamin (G7513, manufactured by Sigma) to RPMI-1640 medium Hepes modification (R5886, manufactured by Sigma). The liquid feeding pump 202 fed the perfusion culture solution from the perfusate bottle 201 into the swine spleen 101 through the tubes 501 and 503 at a flow rate of 10 mL/min.

c) Collecting Section 300

The collecting section 300 is mainly configured to include the tubes 504 and 505 (each C-Flex Pump Tube, product number: 6424-25, manufactured by Yamato Scientific Co. Ltd.) which are connected to the three-way cock 702 (R-type, Cock-specification 360°, TS-TR2K, manufactured by TERUMO CORPORATION), a tube 506 (C-Flex Pump Tube, product number: 6424-25, manufactured by Yamato Scientific Co. Ltd.), and a drainage bottle 301 (2250-0020, manufactured by Thermo Scientific) which is connected to the three-way cock 702 through the tube 506. The perfusion culture solution discharged from the swine spleen 101 entered the three-way cock 702 through the tube 504, and was allowed to flow into the drainage bottle 301 through the tube 506. Switching of the three-way cock 702 enables the perfusion culture solution to be collected from the collection port b through the tube 505 connected to the three-way cock.

d) Imaging Section 400

A video camera (ivis, manufactured by Canon Inc.) for photographing the state of the organ or living tissue 101 (herein, corresponding to the swine spleen) to be perfused was used as the imaging section 400. The use of the imaging section enables the perfusion section 100 to be photographed.

Example 1

Differentiation of MSC Derived from Human Bone Marrow

It was examined whether or not differentiated cells were obtained by introducing mesenchymal stem cells derived from human bone marrow (hereinafter also referred to as "MSC". Promo cell, Lot#: 1080202.3) into the swine spleen 101 using the perfusion culture system produced in Reference Example 1.

First, MSC was cultured in an MSCBM Bullet kit (Lonza) at 3° C. for 24 days. 10% (final concentration) FBS (manufactured by Hyclone), 50-fold diluted Antibiotic-Antimycotic (15240-062, manufactured by Gibco), and 2 mM (final concentration) L-Glutamin (G7513, manufactured by Sigma) were added to RPMI-1640 medium Hepes modification (R5886, manufactured by Sigma) to prepare a perfusate.

The swine spleen 101 was perfused with the resulting perfusate at a flow rate of 10 ml/min. Thirty seconds prior to the introduction of MSC, 10 ml of the perfusate discharged from the swine spleen 101 was collected from the collection port b (this was designated as a fraction NC). The feeding of the perfusate was stopped temporarily by switching the three-way cock 701. Air was injected from the undifferentiated cell introducing port a of the three-way cock 701 into the tube 503 through the syringe. After that, 2 ml of MSC ($3\times10^6$ cells/ml) was injected from the undifferentiated cell introducing port a through the syringe. At this time, in the tube 503, a layer of air which had entered the tube 503 before injecting the MSC solution after stopping the liquid-feeding process was formed between the perfusate and the MSC solution. After the injection of MSC, air was again injected from the undifferentiated cell introducing port a of the three-way cock 701 into the tube 503 through the syringe. After adjusting the flow rate of the perfusate to 10 ml/min, the three-way cock 701 was switched so as to feed the perfusate again. At this time, in the tube 503, a layer of air which had entered the tube 503 before restarting the liquid-feeding process after injecting the MSC solution was formed between the MSC solution and the perfusate at the side of the liquid feeding pump. That is, in the tube 503, the MSC solution was present between the layer of air at the swine spleen 101 side and the layer of air at the liquid feeding pump side. After restarting the liquid-feeding process, MSC was introduced into the swine spleen 101 by continuing the liquid-feeding process until the interface between the MSC solution and the layer of air at the liquid feeding pump side was visually observed to reach the interface between the tube 503 and the artery. After confirming the introduction of MSC, the liquid-feeding process was stopped again. The state was allowed to stand for 3 hours. Thereafter, the perfusion culture was restarted at a flow rate of 10 ml/min. Ten milliliters of the perfusion culture solution discharged from the swine spleen 101 was collected to form six fractions.

Cells obtained by in vitro culturing MSC prior to the introduction into the organ with the perfusate at 37° C. in the presence of 5% carbon dioxide for 3 hours (hereinafter, also referred to as "in vitro-cultured cells"), as well as the six collected fractions, and the cells contained in the fraction NC were washed with PBS and pelletized. RNA was collected from 30 mg of the pellets using an RNeasy mini kit (manufactured by QIAGEN). The collected RNA was subjected to reverse transcription using a High Capacity cDNA synthesis kit (manufactured by ABI) to produce cDNA.

Real-time PCR using the thus produced cDNA and Taqman Gene Expression Assays (ABI Model Nos: Hs00231692_m1, Hs01001343_g1, and Hs01115513_m1) was performed on each of the differentiation markers of MSC (osteoblast differentiation marker Runx2, chondrocyte differentiation marker SOX9, and adipocyte differentiation marker PPARγ) using an ABI7500 device (manufactured by ABI). Real-time PCR of β-actin, which is an endogenous control gene, was performed in the same manner as described above except that primers represented by SEQ ID NOs: 1 and 2 and Taqman probes (SEQ ID NO: 3, manufactured by ABI) in which the 5' terminal was fluorescently labeled with fluorescein (FAM) and the 3' terminal was fluorescently labeled with tetramethyl rhodamine (TAMRA) were used in order to correct the expression levels of mRNA among samples.

Figure 2:
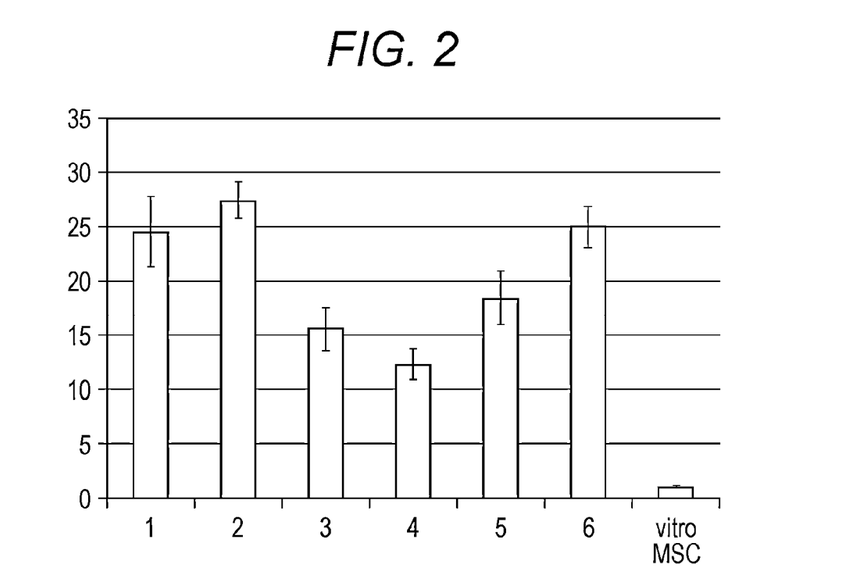
FIG. 2 is a graph showing expression levels of the osteoblast-differentiation marker Runx2 in cells differentiated from MSC, wherein a vertical axis represents the relative expression level (no unit) of Runx2 corrected by β-actin expression, and a horizontal axis represents the number of the collected perfusate fractions, and "vitro MSC" represents cells cultured in vitro.

The results are shown in FIG. 2. FIG. 2 shows the results in which the expression level of Runx2 was corrected using the fraction NC as a background value, and the corrected expression level of Runx2 was normalized with the expression level of β-actin, which is an endogenous control gene. As is clear from FIG. 2, the expression level of osteoblast differentiation marker Runx2 in the cells contained in the six collected fractions was greatly increased, as compared to the expression level of that in the in vitro-cultured cells. The measurement of the expression levels of SOX9 and PPARγ was attempted in the same manner as in Runx2. However, the expression of chondrocyte differentiation marker SOX9 and the expression of adipocyte differentiation marker PPARγ could not be detected. This result showed that the osteoblast differentiation of MSC was induced.

Example 2

Differentiation of Megakaryocyte-Induced K562 Cells and Production of Platelets

It was examined whether or not differentiation of megakaryocyte-induced K562 cells and production of platelets by introducing megakaryocyte-induced K562 cells into the swine spleen 101 using the perfusion culture system produced in the manner described in Reference Example 1.

First, K562 cells (human chronic myelogenous leukemia cell lines; ATCC, CCL-243) were cultured in a culture solution prepared by adding 10% (final concentration) FBS (fetal calf serum, manufactured by Hyclone), 100-fold diluted Antibiotic-Antimycotic (15240-062, manufactured by Gibco), 5 µM (final concentration) SB202190 (S7067, manufactured by Sigma), and 10 ng/µl (final concentration) PMA (phorbol 12-myristate 13-acetate, P1585, manufactured by Sigma) to RPMI-1640 (R8758, manufactured by Sigma) for 3 days, which resulted in differentiation of megakaryocytes. The cells are designated as megakaryocyte-induced K562 cells. The megakaryocyte-induced K562 cells were stained with CFSE (341-06443, manufactured by DOJINDO LABORATORIES) before the introduction into the swine spleen.

The swine spleen 101 was perfused with the perfusate at a flow rate of 10 ml/min. Thirty seconds prior to the introduction of megakaryocyte-induced K562 cells, 10 ml of the perfusate discharged from the swine spleen 101 was collected from the collection port b (this was designated as a fraction NC). The feeding of the perfusate was stopped temporarily by switching the three-way cock 701. Air was injected from the undifferentiated cell introducing port a of the three-way cock 701 into the tube 503 through the syringe. After that, 10 ml of megakaryocyte-induced K562 cells ($2 \times 10^6$ cells/ml) was injected from the undifferentiated cell introducing port a through the syringe. At this time, in the tube 503, a layer of air which had entered the tube 503 before injecting the megakaryocyte-induced K562 cell solution after stopping the liquid-feeding process was formed between the perfusate and the megakaryocyte-induced K562 cell solution. After the injection of megakaryocyte-induced K562 cells, air was again injected from the undifferentiated cell introducing port a of the three-way cock 701 into the tube 503 through the syringe. After adjusting the flow rate of the perfusate to 10 ml/min, the three-way cock 701 was switched so as to feed the perfusate again. At this time, in the tube 503, a layer of air which had entered the tube 503 before restarting the liquid-feeding process after injecting the megakaryocyte-induced K562 cell solution was formed between the megakaryocyte-induced K562 cell solution and the perfusate at the side of the liquid feeding pump. That is, in the tube 503, the megakaryocyte-induced K562 cell solution was present between the layer of air at the swine spleen 101 side and the layer of air at liquid feeding pump side. After restarting the liquid-feeding process, the megakaryocyte-induced K562 cell solution was introduced into the swine spleen 101 by continuing the liquid-feeding process until the interface between the megakaryocyte-induced K562 cell solution and the layer of air at the liquid feeding pump side was visually observed to reach the interface between the tube 503 and the artery. After confirming the introduction of megakaryocyte-induced K562 cells, the liquid-feeding process was stopped again. The state was allowed to stand for 15 hours. Thereafter, the perfusion culture was restarted at a flow rate of 10 ml/min. Thirty milliliters of the perfusion culture solution discharged from the swine spleen 101 was collected to form three fractions. After collecting the perfusion culture solution, the swine spleen was collected and sliced into sections.

Ten milliliters of the collected perfusion culture solution was centrifuged at 200 g for 5 minutes. PRP (Platelet Rich Plasma) was recovered by collecting the supernatant. The PRP was washed with 10 ml of PBS and suspended in 1 ml of PBS/1% BSA solution. Then, the fluorescent signal of CFSE in the platelet-sized fractions was measured with FACS Calibur (manufactured by Becton, Dickinson and Company).

Figure 3:
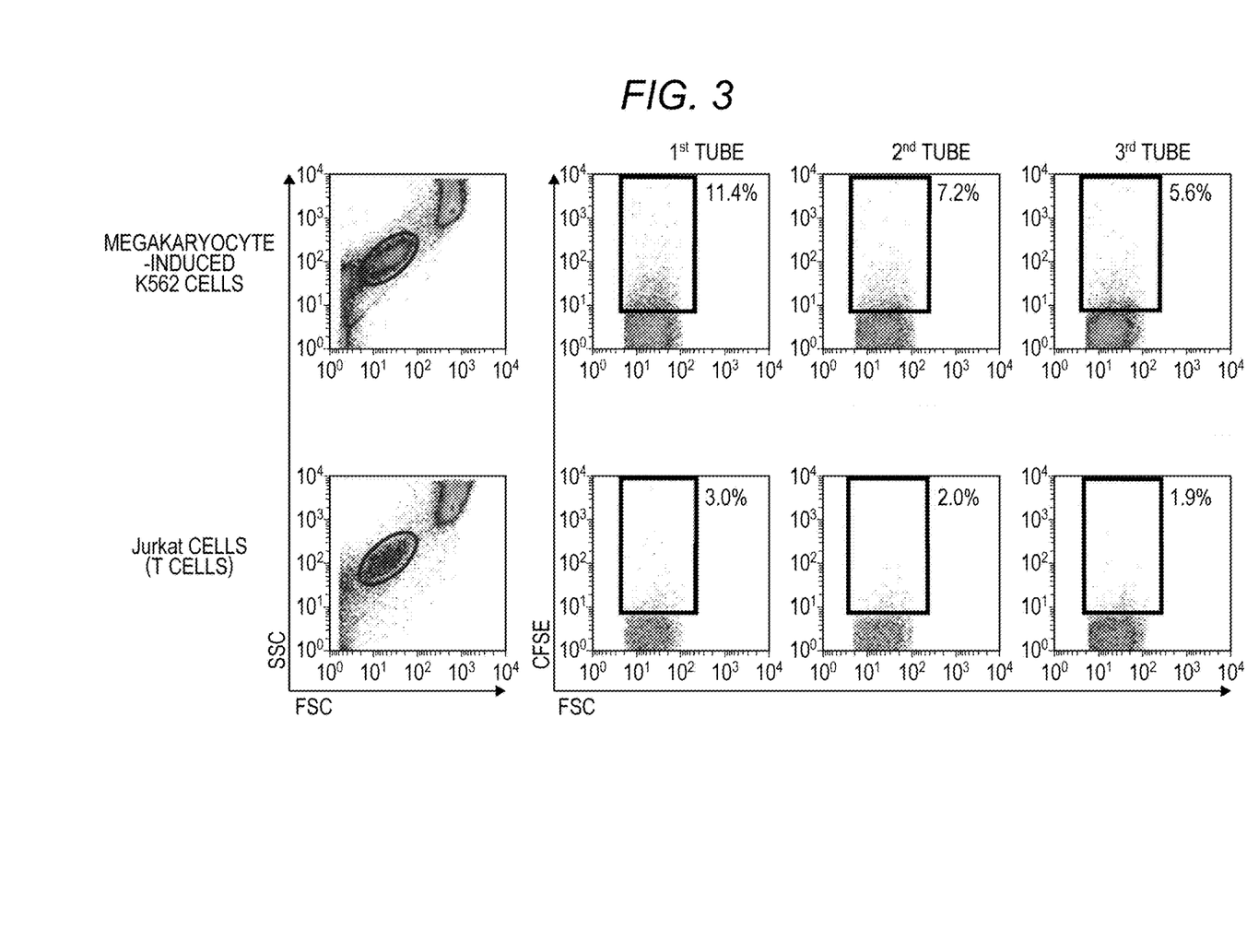
FIG. 3 shows the results of FACS analysis using the platelet-sized fractions in the collected perfusion culture supernatant.

The results are shown in FIG. 3. As is clear from FIG. 3, in the case where megakaryocyte-induced K562 cells were introduced, the fluorescent signal of CFSE was detected from platelet-sized fractions in the collected perfusion culture solution. In the case where Jurkat cells (ATCC, TIB-152), i.e., human acute T cell leukemia cell lines not producing platelets in the cell lineage, were introduced, the number of the fluorescent signal of CFSE detected from platelet-sized fractions in the collected perfusion culture solution was significantly fewer than that in the case where megakaryocyte-induced K562 cells were introduced. In the case where the fraction NC was measured in the same manner as described above, no fluorescent signal was detected.

Figure 4:
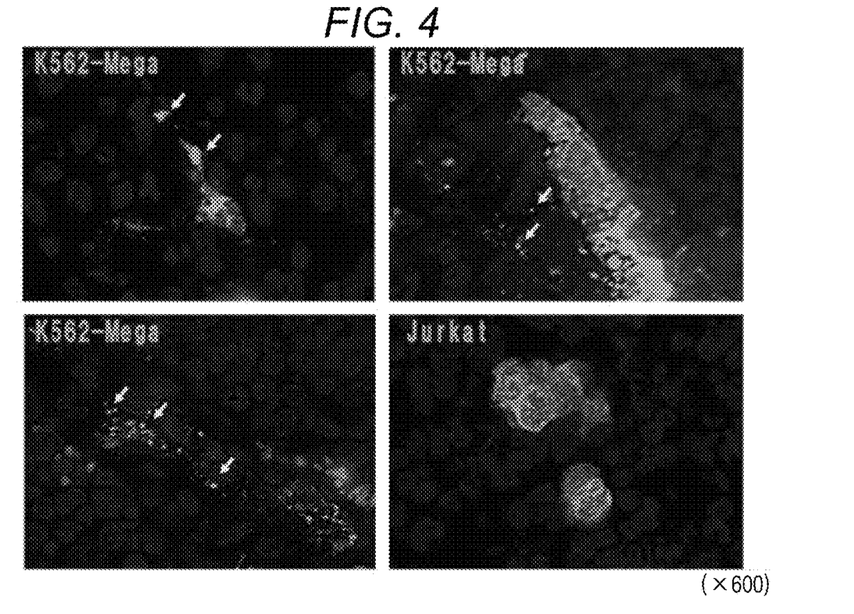
FIG. 4 shows fluorescence micrographs of platelets released from megakaryocyte-induced K562 cells.

The prepared sections were observed with a fluorescence microscope (BZ-9000, manufactured by KEYENCE CORPORATION). The results are shown in FIG. 4. The arrows of FIG. 4 indicate that platelets were released from the introduced megakaryocyte-induced K562 cells.

Figure 5:
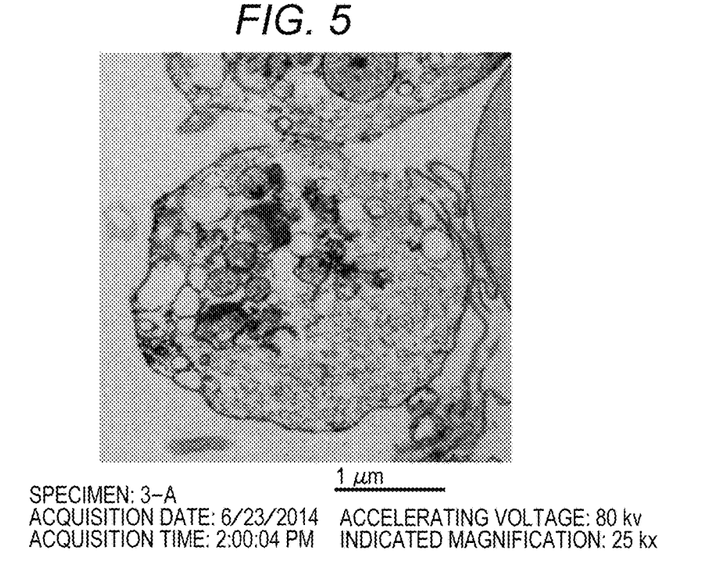
FIG. 5 is a transmission electron micrograph of the collected platelets.

Ten milliliters of the collected perfusion culture solution was centrifuged at 200 g for 5 minutes. PRP was recovered by collecting the supernatant. The PRP was washed with 10 ml of PBS, and suspended in 1 ml of glutaraldehyde (GA) fixative. The resulting suspension was observed with a transmission electron microscope (H-7500, manufactured by Hitachi, Ltd.). The results are shown in FIG. 5. As shown in FIG. 5, specific internal structures were confirmed in platelets (granules and open canaliculi). The collected particles were identified as platelets.

Example 3

Relationship Between Lactate Dehydrogenase Activity Value in Perfusate and Differentiation Potency of Swine Organ As for swine spleen sections having a time lag between the extraction to the introduction of cells, the lactate dehydrogenase activity in the perfusate and the amount of differentiation-induced products were measured using the organ perfusion culture system produced in the manner described in Reference Example 1.

The swine spleen sections on the day, after one day, and after three days of the extraction were placed in the organ perfusion culture system of FIG. 1. Physiological saline was perfused at a flow rate of 10 mL/min for 3 hours, and then the perfusate was perfused at a flow rate of 10 mL/min for 1 hour. Thirty seconds prior to the introduction of megakaryocytes fluorescently stained with CFSE, 10 ml of the perfusate discharged from the swine spleen 101 was collected from the collection port b. The liquid-feeding process of the perfusate was stopped temporarily by switching the three-way cock 701. The megakaryocyte ($3 \times 10^6$ cells) solution fluorescently stained with CFSE was injected from the undifferentiated cell introducing port a through the syringe. The state was allowed to stand for about 12 hours. Thereafter, the perfusion was restarted at a flow rate of 10 ml/min. Ten milliliters of the perfusion culture solution discharged from the swine spleen 101 was collected to form six fractions.

The perfusate collected before the introduction of megakaryocytes was pulverized with a centrifugal vacuum concentrator (Spin Dryer mini VC-155, manufactured by TITEC Corporation). PBS was added to the resulting powder so as to be 20-fold concentrated. A reaction solution of LDH Cytotoxicity DetectionKit (manufactured by TAKARA) was added to the concentrated solution. The absorption at 490 nm of the reaction solution was measured with an absorptiometer (VERSAmix, Molecular Devices). Thus, the activity of LDH was determined.

The solution collected after being allowed to stand was replaced with PBS/1% BSA, followed by analysis using FACS Verse (BD Biosciences). The fraction having the same size as that of platelet and showing staining of CFSE was counted as a platelet-like particle.

Figure 6:
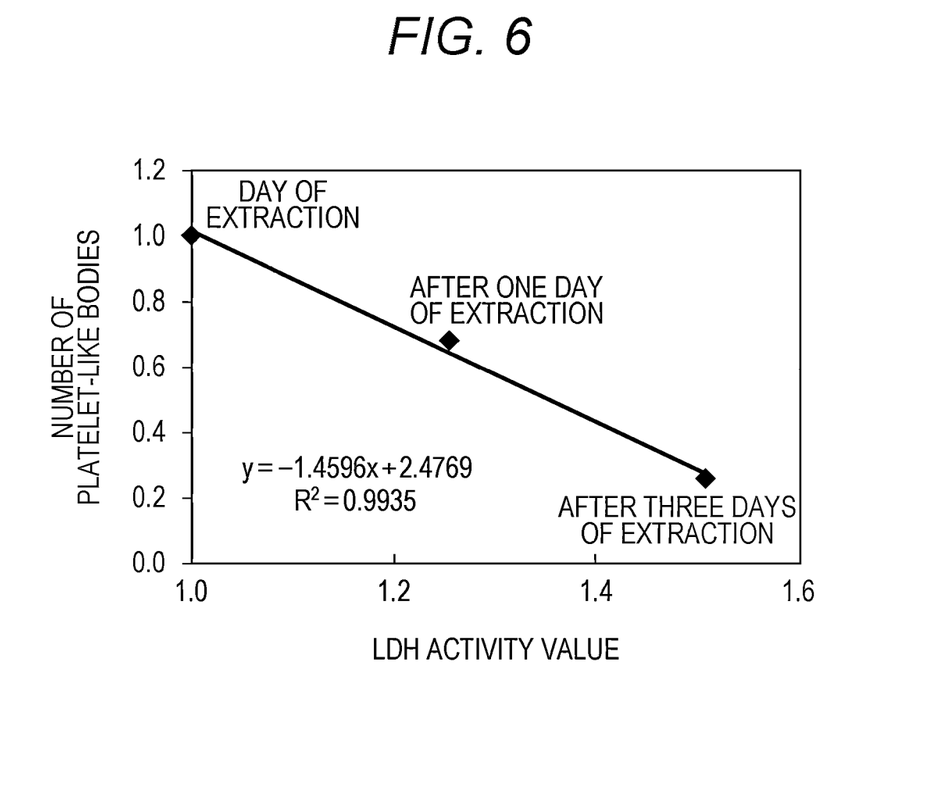
FIG. 6 is a graph showing a relationship between the number of the collected platelet-like particles in the perfusate and the activity of lactate dehydrogenase.

In FIG. 6, the lactate dehydrogenase activity in the perfusate and the proportion of platelet-like particles before the introduction of megakaryocytes regarding swine spleen sections on the day, after one day, and after three days of the extraction are shown, defining the day of the extraction as 1. It was confirmed that the number of platelet-like particles changed depending on the lactate dehydrogenase activity. The lactate dehydrogenase activity was determined to be effective as an indicator showing the differentiation-inducing properties of the swine spleen.

What is claimed is:

1. A method for obtaining differentiated cells and/or differentiated cell products, comprising the steps of:
   introducing undifferentiated cells into a perfused living organ or a perfused living tissue, wherein the living organ or living tissue is a living organ or living tissue extracted from an animal other than humans;
   subjecting the undifferentiated cells to perfusion culture together with the living organ or living tissue so as to allow the undifferentiated cells to differentiate;
   collecting a perfusion culture solution comprising the resulting differentiated cells and/or differentiated cell products, wherein the resulting differentiated cells are cells which were differentiated from the undifferentiated cells in the living organ or living tissue in the subjecting step, and wherein the differentiated cell products are products which were produced by the cells differentiated from the undifferentiated cells in the living organ or living tissue in the subjecting step; and obtaining the differentiated cells and/or differentiated cell products comprised in the collected perfusion culture solution,
wherein the differentiated cells are allogeneic to the living organ or living tissue.

2. The method according to claim 1, wherein the undifferentiated cells are human-derived cells.

3. The method according to claim 1, wherein the undifferentiated cells are stem cells or precursor cells.

4. The method according to claim 3, wherein the stem cells are at least one selected from the group consisting of ES cells, cloned ES cells, mesenchymal stem cells, and iPS cells.

5. The method according to claim 3, wherein the precursor cells are at least one selected from the group consisting of platelet precursor cells, liver precursor cells, heart precursor cells, and neuronal precursor cells.

6. The method according to claim 5, wherein the platelet precursor cells are at least one selected from the group consisting of megakaryocyte precursor cells, megakaryoblasts, and promegakaryocytes.

7. The method according to claim 5, wherein the liver precursor cells are at least one selected from the group consisting of hepatoblasts, hepatic precursor cells, hepatic stellate precursor cells, hepatic stem/precursor cells, vascular endothelial precursor cells from liver, and mesothelial precursor cells from liver.

8. The method according to claim 5, wherein the heart precursor cells are cardiac muscle precursor cells or vascular endothelial precursor cells from heart.

9. The method according to claim 5, wherein the neuronal precursor cells are at least one selected from the group consisting of neuron precursor cells, glial precursor cells, and vascular endothelial precursor cells from central nervous system.

10. The method according to claim 1, wherein the living organ or living tissue is at least one selected from the group consisting of spleen, liver, pancreas, heart, lung, kidney, and bone.

11. The method according to claim 10, wherein the living organ or living tissue is spleen, and the differentiated cells are mature megakaryocytes and/or osteoblasts.

12. The method according to claim 10, wherein the living organ or living tissue is bone, the differentiated cells are mature megakaryocytes, and the differentiated cell products are platelets.

13. The method according to claim 1, wherein the introduction step is performed by adding the undifferentiated cells to a perfusate.

14. The method according to claim 1, further comprising the step of determining whether or not the introduction step is performed by evaluating a storage state of the living organ before the introduction step.

15. The method according to claim 14, wherein in the determination step the storage state of the living organ is evaluated by measuring at least one selected from lactate dehydrogenase in the perfusate, lactic acid in the perfusate, perfusion pressure, and dissolved oxygen.

16. A method of perfusion culture with a perfusion culture system using a perfused living organ or a perfused living tissue, comprising the steps of:
measuring an activity of lactate dehydrogenase of a perfusate on a day the living organ or the living tissue is extracted, the extracted living organ or living tissue being placed in the perfusate;
introducing undifferentiated cells into the perfused living organ or the perfused living tissue;
subjecting the undifferentiated cells to perfusion culture together with the living organ or living tissue so as to allow the undifferentiated cells to differentiate;
collecting a perfusion culture solution comprising the resulting differentiated cells and/or differentiated cell products, wherein the resulting differentiated cells are cells which were differentiated from the undifferentiated cells in the living organ or living tissue in the subjecting step, and wherein the differentiated cell products are products which were produced by the cells differentiated from the undifferentiated cells in the living organ or living tissue in the subjecting step; and
obtaining the differentiated cells and/or differentiated cell products comprised in the collected perfusion culture solution,
wherein the differentiated cells are allogeneic to the living organ or living tissue.

17. A method of perfusion culture with a perfusion culture system using a perfused living organ or a perfused living tissue, comprising the steps of:
introducing platelet precursor cells into a perfused living organ or a perfused living tissue, the living organ or the living tissue being extracted from an animal other than humans and placed in a perfusion culture solution in a container of the perfusion culture system, the living organ being selected from the group consisting spleen, liver, pancreas, lung and kidney, the living tissue being a bone;
subjecting the platelet precursor cells to perfusion culture together with the living organ or living tissue in the perfusion culture solution in the container so as to allow the undifferentiated cells to differentiate into megakaryocytes producing platelets;
collecting the perfusion culture solution comprising the platelets from the living organ or living tissue, wherein the platelets are products which were produced by the megakaryocytes differentiated from the platelet precursor cells in the subjecting step; and
obtaining the platelets comprised in the collected perfusion culture solution.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ccacactgtg cccatctacg                                              20

<210> SEQ ID NO 2
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 2
aggatcttca tgaggtagtc agtcag                                       26

<210> SEQ ID NO 3
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 3
atgccctccc ccatgccatc ctgcgt                                       26
```